United States Patent [19]

Rollison et al.

[11] Patent Number: 5,076,790
[45] Date of Patent: Dec. 31, 1991

[54] METHOD FOR RECORDING DENTAL BITE REGISTRATION

[76] Inventors: Derward F. Rollison; Georgia S. Rollison, both of 56 Lakeview Park Dr., Colonial Heights, Va. 23834

[21] Appl. No.: 678,714

[22] Filed: Apr. 1, 1991

[51] Int. Cl.⁵ ............................................. A61C 9/00
[52] U.S. Cl. ...................................... 433/214; 433/71
[58] Field of Search .................... 433/71, 214, 215, 48

[56] References Cited

U.S. PATENT DOCUMENTS

| 4,445,856 | 5/1984 | Sturtzkopf | 433/71 |
|---|---|---|---|
| 4,543,372 | 9/1985 | Watanabe et al. | 523/109 |
| 4,626,558 | 12/1986 | Pellico | 523/109 |
| 4,670,053 | 6/1987 | Kooke et al. | 106/35 |
| 4,836,853 | 6/1989 | Gribi | 106/35 |
| 4,979,989 | 12/1990 | Ridoux | 106/35 |

Primary Examiner—John J. Wilson
Assistant Examiner—Cindy A. Cherichetti
Attorney, Agent, or Firm—Norman B. Rainer

[57] ABSTRACT

A method for producing a dental bite registration involves the utilization of an alginate dental impression powder composition. The composition is mixed with water in an amount considerably less than the amount of water that would be used for dental impression purposes, and the temperature of the water employed is higher than the temperature of water that would be employed for dental impression purposes. The mixture of the powder composition with water is rapidly blended to form a homogenous lump of dough-like consistency which will not sag but which undergoes plastic deformation. Upon insertion into the oral cavity to record bite registration, the lump hardens in 3-4 minutes.

2 Claims, No Drawings

METHOD FOR RECORDING DENTAL BITE REGISTRATION

BACKGROUND OF THE INVENTION

1. Field of the Invention

This invention is in the field of dentistry, and more particularly concerns an improved process for recording the bite registration of a dental patient.

2. Description of the Prior Art

In conducting remedial, restorative or prosthetic procedures involving structural modifications of teeth, an impression or casting is made to record the original configuration of the teeth. It is also important that the bite registration be recorded so as to know the exact interaction of the upper and lower teeth.

Alginate compositions are generally employed in present practice for making dental impressions in order to fabricate dental prosthesis of correct size and shape. As described in U.S. Pat. Nos. 4,543,372; 4,836,853 and elsewhere, the alginate composition is a powder mixture comprised of a water soluble salt of alginic acid such as sodium alginate, a gelling agent such as calcium sulfate dihydrate, a gelation control agent such as sodium phosphate, and fillers such as fine particle powders of diatomaceous earth, talc and pearlite.

At the time of use, water is mixed with the alginate powder composition in a weight ratio of powder to water of about 0.35 to 0.4. The mixture is rapidly blended to form a homogeneous paste. The paste is then put on a tray for impression, and the tray is introduced into the oral cavity of the patient and pressed onto those teeth from which it is desired to copy an impression. After the paste has gelled to form a hard elastic material, it is removed. The period of time required for gelation is about 3 to 4 minutes, particularly if the temperature of the water employed to make the paste is between about 60 and 70 degrees F.

Bite registration recordings are generally made employing a thermally softened wax. However, the use of wax, which is applied in softened condition and caused to solidify by cooling in place, permits some movement of the teeth during the solidification process.

It is accordingly an object of the invention to provide an improved method for producing a bite registration recording.

It is another object of this invention to produce a method as in the foregoing object which utilizes materials that have already found widespread acceptance for use in the oral cavity.

It is a further object of the present invention to provide a method of the aforesaid nature which is rapid and produces an accurate bite registration recording at a cost comparable to earlier methods.

These objects and other objects and advantages of the invention will be apparent from the following description.

SUMMARY OF THE INVENTION

The above and other beneficial objects and advantages are accomplished in accordance with the present invention by a method for producing a dental bite registration comprising:

a) mixing an alginate powder dental impression composition and water, employing a weight ratio of powder/water in the range of 0.65 to 0.75, said water being at a temperature in the range of 75 to 80 degrees F., b) kneading said mixture to form a homogeneous elongated lump whose consistency is such as to be shape-retaining yet amenable to plastic deformation, c) inserting said lump into the oral cavity and positioning it with respect to the teeth of interest, d) causing the patient to bite into said lump, e) waiting 3-4 minutes, during which time the lump hardens to a non-deformable structure, and h) removing said hardened structure from the oral cavity.

DESCRIPTION OF THE PREFERRED EMBODIMENT

Suitable alginate dental impression powder compositions useful in the practice of the present invention are generally available from different manufacturers, one such manufacturer being Dentsply International, Inc. of York, Pa. A typical alginate impression powder composition may be comprised as follows:

| Component | Parts by Weight |
| --- | --- |
| Sodium Alginate | 15 |
| Calcium Sulfate Dihydrate | 15 |
| Trisodium Phosphate | 2 |
| Diatomaceous Earth | 60 |
| Talc | 5 |
| Potassium Titanium Fluoride | 1 |
| Aluminum Oxide | 2 |
| Polyvinylpyrrolidone | 0.9 |

The initial mixing of the powder with water is preferably done in a rubber bowl employing a spatula. In the final stage of mixing, the composition has a dough-like or putty-like consistency and is preferably homogenized by hand kneading and rolling. The elapsed time from the initial contact of the powder with the water to formation of a homogeneous lump of dough-like consistency should be no more than about 40 seconds.

Once emplaced in the oral cavity, the composition hardens within 3 to 4 minutes. It has been discovered that, during the hardening period, less shifting movement of the patient's teeth can occur than in the case of the use of the older wax compositions. Consequently, a more accurate bite registration recording is produced. Removal of the hardened composition from the teeth is no more difficult than the removal of older wax materials. By virtue of the unusually high value of the powder/water ratio employed in the practice of this invention, and the use of higher than usual water temperatures, the necessary dough-like consistency is rapidly achieved wherein the composition will not sag, yet will undergo plastic deformation. The setting time of 3-4 minutes is comparable to setting times required by softened wax in the older methods.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A method for producing a dental bite registration comprising:

a) mixing an alginate powder dental impression composition and water, employing a weight ratio of powder/water in the range of 0.65 to 0.75, said water being at a temperature in the range of 75 to 80 degrees F., b) kneading said mixture to form a homogenous elongated lump whose consistency is such as to be shape-retaining yet amenable to plastic deformation, c) inserting said lump into the oral cavity and positioning it with respect to the teeth of interest, d) causing the patient to bite into said lump, e) waiting 3-4 minutes, during which time the lump hardens to a non-deformable structure, and h) removing said hardened structure from the oral cavity.

2. The method of claim 1 wherein the elapsed time from the initial contact of the powder with water to formation of said lump is no more than 40 seconds.

* * * * *